US010591428B2

(12) United States Patent
Gwenin et al.

(10) Patent No.: US 10,591,428 B2
(45) Date of Patent: Mar. 17, 2020

(54) SENSORS

(71) Applicant: Bangor University, Bangor (GB)

(72) Inventors: Chris David Gwenin, Bangor (GB); Jennifer Helen Halliwell, Menai Bridge (GB)

(73) Assignee: BANGOR UNIVERSITY, Bangor (GB)

( * ) Notice: Subject to any disclaimer, the term of this patent is extended or adjusted under 35 U.S.C. 154(b) by 968 days.

(21) Appl. No.: 14/298,551

(22) Filed: Jun. 6, 2014

(65) Prior Publication Data

US 2014/0363894 A1     Dec. 11, 2014

(30) Foreign Application Priority Data

Jun. 6, 2013 (GB) .................. 1310090.4

(51) Int. Cl.
*G01N 33/68* (2006.01)
*G01N 27/02* (2006.01)
*G01N 33/543* (2006.01)

(52) U.S. Cl.
CPC ....... *G01N 27/026* (2013.01); *G01N 33/5438* (2013.01); *G01N 2333/33* (2013.01)

(58) Field of Classification Search
CPC ............. G01N 27/026; G01N 2333/33; G01N 33/5438
USPC ...................... 436/86; 422/82.05; 204/403.1; 205/777.5
See application file for complete search history.

(56) References Cited

U.S. PATENT DOCUMENTS

| 2005/0003396 | A1 | 1/2005 | Ozkan et al. |
| 2007/0116600 | A1* | 5/2007 | Kochar .................. G01N 21/76 422/65 |
| 2009/0253149 | A1* | 10/2009 | Ahrens .................. C12Q 1/003 435/7.4 |

FOREIGN PATENT DOCUMENTS

| GB | 2 350 677 A | 12/2000 |
| WO | 2004/031355 A2 | 4/2004 |
| WO | 2005/076785 A2 | 8/2005 |
| WO | 2009/035476 A1 | 3/2009 |
| WO | 2009/052422 A1 | 4/2009 |

OTHER PUBLICATIONS

Dong et al., "Using fluorescent sensors to detect botulinum neurotoxin activity in vitro and in living cells," *PNAS* 101(41):14701-14706 (2004).
Ferracci et al., "A label-free biosensor assay for botulinum neurotoxin B in food and human serum," *Analytical Biochemistry* 410:281-288 (2011).

(Continued)

*Primary Examiner* — Rebecca M Fritchman
(74) *Attorney, Agent, or Firm* — Christopher S. Dodson; Nexsen Pruet, PLLC

(57) ABSTRACT

The present invention relates to a sensor for detecting the presence of a botulinum neurotoxin in a sample, the sensor comprising: (a) an electrically conductive substrate coated with at least one SNAP-25, VAMP or syntaxin protein; and (b) a detection arrangement adapted to enable the detection of the cleavage of at least one SNAP-25, VAMP or syntaxin protein by the botulinum neurotoxin. The invention also relates to methods of making a sensor, methods of detecting and a detection kit for botulinum neurotoxin.

14 Claims, 3 Drawing Sheets

(56) References Cited

OTHER PUBLICATIONS

Sapsford et al., "A fluorescence detection platform using spatial electroluminescent excitation for measuring botulinum neurotoxin A activity," *Biosensors and Bioelectronics* 24:618-625 (2008).
Hutter et al. "Gold-nanoparticle-based biosensors for detection of enzyme activity," *Trends in Pharmacological Sciences* 34(9):497-507 (Sep. 2013).
Pan et al., "Colorimetric detection of apoptosis based on caspase-3 activity assay using unmodified gold nanoparticles," *Chem. Commun.* 48:997-999 (2012).

* cited by examiner

SENSORS

TECHNICAL FIELD OF THE INVENTION

The invention relates to a sensor and methods for detecting (and optionally quantifying) botulinum neurotoxin in a sample.

BACKGROUND TO THE INVENTION

Botulinum neurotoxins are one of the most potent toxins known to man with an $LD_{50}$ of 1-5 ng/kg of body mass when administered intravenously (F. Gessler, et al, (2007) *Diagnostic Microbiology and Infectious Disease*, 57, 243-249). The toxin is also produced as a pharmaceutical product to treat conditions such as blepharospasm and hemifacial spasm (R. L. Rosales, et al., (2006) *European Journal of Neurology*. 13, 2-10) in addition to being used in certain cosmetic procedures. The current method of determining the presence and concentration of the toxin is via mouse bioassay. This method is used due to its ability not only to detect the toxin but to establish whether the sample is active. However, mouse trials are not only expensive, but can also inflict suffering to the animal. Furthermore, these trials are time consuming and not suited to testing in remote locations.

The quantification of the active contents of the botulinum toxin is of paramount importance for therapeutic applications and, to date, no reliable method has been developed which does not have the requirement of a mouse trial for obtaining or ascertaining the correct dosage of botulinum toxin.

It is an object of the present invention is to provide a sensor and/or method which can be reliably and easily used to identify the presence of botulinum toxin in a sample. It would be preferred that the sensor and/or method could additionally or alternatively be used to quantify the botulinum toxin in a sample. Furthermore, it would be preferable that any such sensor and/or method could be used to negate the use of mice and suitable for remote testing of samples outside of the laboratory environment.

SUMMARY OF THE INVENTION

In accordance with a first aspect of the present invention, there is provided a sensor for detecting the presence of a botulinum neurotoxin in a sample, the sensor comprising:

(a) an electrically conductive substrate coated with at least one synaptosomal-associated protein-25 (SNAP-25), vesicle-associated membrane protein (VAMP) or syntaxin protein; and (b) a detection arrangement adapted to enable the detection of the cleavage of at least one SNAP-25, VAMP or syntaxin protein by the botulinum neurotoxin.

Preferably the electrically conductive substrate is coated with a plurality of SNAP-25, VAMP or syntaxin proteins and/or mixtures thereof. More preferably the majority or entire exposed surface of the electrically conductive substrate is coated with a plurality of SNAP-25, VAMP or syntaxin proteins and/or mixtures thereof.

The sensor may allow for the detection of the quantity of botulinum neurotoxin in a sample by detecting the quantity of SNAP-25, VAMP or syntaxin proteins cleaved by the botulinum neurotoxin in the sample. In this way, the sensor not only detects the presence of the toxin in a sample, but is also able to provide an indication as to concentration or quantity of toxin. For example, the sensor may be able to ascertain if a food sample contains an acceptable trace quantity or a lethal dose of the toxin.

In one of the embodiments, the electrically conductive substrate may comprise particles. It will be apparent to the skilled addressee that the particles can be nanoparticles or colloidal. It is preferred that these particles are negatively charged and suspended in a salt solution and the detection arrangement comprises a visual change of colour of the buffer or precipitation of the particles due to the cleavage of one or more SNAP-25, VAMP or syntaxin proteins. The term 'visual' it is intended to mean that change of colour is discernable to the human eye. A colour chart may be provided to be used in conjunction with the sensor so that the user can easily calibrate the total colour change which has taken place so as to provide confirmation of quantity of toxin in a sample. The colour change may be from a red to a blue colour absorbing in the 525-670 nm region. The negative charge of the particles cause them to repel each other in solution staying red in colour absorbing at 525 nm. When a salt is added to uncoated particles, this neutralises the charges causing them to clump together turning blue in colour. When a sample containing the toxin is added to the solution containing the particles, a portion of SNAP-25, VAMP or syntaxin is cleaved off, resulting in reduced protection for the particles allowing for aggregation of the particles which turn blue and which can be detected by the human eye and/or an optical device.

In another embodiment of the present invention, the electrically conductive substrate may comprise one or more electrodes. It is envisaged that such electrodes will be operably connected to some form of circuitry so that the impedance of the electrodes can be assessed. It is preferred that the electrodes are housed within an electrochemical cell and the detection arrangement comprises an impedance measuring device (or circuitry) for measuring the change of impedance after incubating the sample with the electrodes in order to assess cleavage of one or more SNAP-25, VAMP or syntaxin proteins bound to the electrodes.

The change of impedance may be measured with reference to a control. Such a control may comprise a redox probe. In the alternative, the control impedance may have already been established and this set as a reference parameter in the impedance measuring device.

In accordance with another aspect of the present invention, there is provided a method of producing a sensor for detecting the presence of a botulinum neurotoxin in a sample, the method comprising:

(a) coating an electrically conductive substrate with a plurality of SNAP-25, VAMP or syntaxin proteins and/or mixtures thereof so as to form conjugates;

(b) providing a vessel in which the conjugates can be placed in contact with the sample and optionally other reagents; and (c) providing a detection arrangement adapted to enable the detection of botulinum neurotoxin driven SNAP-25, VAMP or syntaxin cleavage events.

The detection arrangement may comprise a detector and the method may further comprise:

(d) coupling the detector to a display for displaying the presence, and optionally the quantity, of the botulinum neurotoxin in the sample.

In accordance with a further aspect of the present invention, there is provided a method of detecting the presence of a botulinum neurotoxin in a sample, the method comprising:

(a) providing an electrically conductive substrate coated with at least one SNAP-25, VAMP or syntaxin protein so as to form a conjugate;

(b) contacting the sample with the conjugate; and (c) detecting the cleavage of the at least one SNAP-25, VAMP or syntaxin protein on the conjugate by the botulinum neurotoxin if present in the sample.

The electrically conductive substrate may be coated with a plurality of SNAP-25, VAMP or syntaxin proteins and/or mixtures thereof. The method may further comprise the step of:

(d) quantifying the botulinum neurotoxin in the sample by detecting the number or quantity of SNAP-25, VAMP or syntaxin proteins which have been cleaved.

In one embodiment, the electrically conductive substrate may comprise particles and the cleavage of the SNAP-25, VAMP or syntaxin proteins is by a visual change of colour of the buffer or precipitation of the particles. The detection of the cleavage may be by detecting and measuring the difference in absorbance profile between 525-670 nm relative to a control absorbance profile. The control absorbance profile may be provided by a physical control reagent or buffer solution or as a pre-determined parameter.

In another embodiment, the electrically conductive substrate may comprise electrically conductive electrodes housed within an electrochemical cell and the cleavage of the SNAP-25, VAMP or syntaxin protein may be detected by measuring the change of impedance profile relative to a control impedance profile. Again, the control impedance profile may be provided by means of a control reagent (such as a redox probe) or as a pre-determined parameter.

In accordance with a yet another aspect of the present invention, there is a detection kit for detecting the presence of a botulinum neurotoxin in a sample, the kit comprising:

(a) an electrically conductive substrate coated with at least one SNAP-25, VAMP or syntaxin protein;

(b) a detection arrangement adapted to enable the detection of the cleavage of the at least one SNAP-25, VAMP or syntaxin protein by the botulinum neurotoxin.

The kit may further comprise a detector for detecting the cleavage of the at least one SNAP-25, VAMP or syntaxin protein by the botulinum neurotoxin; and (c) a display for detection of displaying the detection of the cleavage of the at least one SNAP-25, VAMP or syntaxin protein.

The electrically conductive substrate may be coated with a plurality of SNAP-25, VAMP or syntaxin proteins and/or mixtures thereof and have a detector capable of detecting the number or quantity of SNAP-25, VAMP or syntaxin proteins which have been cleaved so as to provide an indication of the concentration of toxin in the sample.

In one related embodiment, the electrically conductive substrate of the kit comprises negatively charged electrically conductive particles suspended in a buffer solution and the detector comprises a detection arrangement adapted to enable the detection of the cleavage of one or more SNAP-25, VAMP or syntaxin proteins. Such a detection arrangement may be a visual change of colour of the buffer or precipitation of the particles due to the cleavage of one or more SNAP-25, VAMP or syntaxin proteins and in such instance a colour chart may be provided with the kit so as to be used in conjunction with the sensor to enable the user to easily calibrate the total colour change which has taken place so as to provide confirmation of the existence and/or quantity of toxin in a sample. In the alternative or additionally, the kit may comprise an optical measuring device for assessing the absorbance profile of the combined solution and sample between 525-670 nm. Such a measuring device may be coupled to a display device which may also be provided with the kit so as to easily convey to the user, the presence or absence of the toxin in a sample.

In another related embodiment, the electrically conductive substrate of the kit comprises electrically conductive electrodes in an electrochemical cell and the detector comprises an impedance measuring device for assessing the impedance profile of the electrodes after incubation with the sample.

In all aspects of the invention, it is preferred that the electrically conductive particles or electrodes comprise gold, silver, copper, iron or nickel. It is most preferred that the particles or electrodes comprise gold. Furthermore, a number of methods of attaching the proteins to the electrically conductive particles may be utilised. For SNAP-25, simple incubation of the protein with the electrically conductive substrate allows for the formation of a monolayer by means of the cysteine residues. For VAMP and syntaxin, modification of the sulphur on the methionine side chain would allow layers of proteins to be formed on the electrically conductive substrate.

The present invention not only provides for an effective and quick sensor and method of detecting botulinum neurotoxin, but also a way of additionally quantifying the concentration of toxin in a given sample.

DETAILED DESCRIPTION OF THE INVENTION

Embodiments of the present invention will now be described, by way of example only, with reference to the accompanying figures, in which.

The invention can be employed utilising two related assays which utilise the endopeptidase nature of the toxin to determine the amount and activity of the toxin within a sample. Both assays utilise the fact that the toxin cleaves a portion of the protein SNAP-25 (synaptosomal-associated protein-25). In essence a monolayer of SNAP-25 is formed on a gold surface and the change in the layer coverage after cleavage by the toxin is monitored thereby producing a positive indication if the toxin is present in the sample and the number of SNAP-25 proteins cleaved monitored in order to provide a quantitative indication of the toxin.

Figure 1:
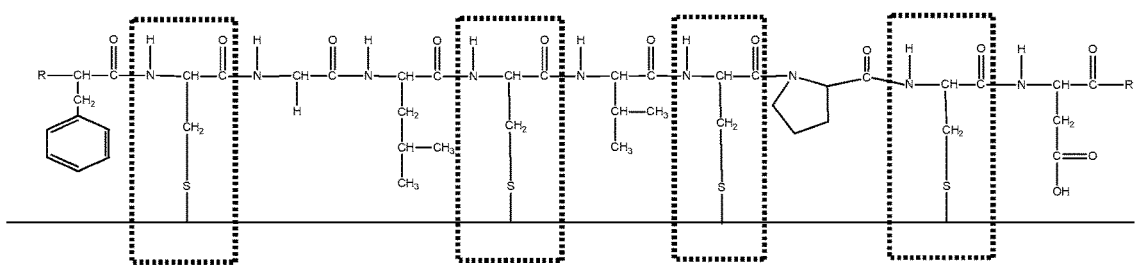
FIG. 1 is a diagram illustrating a section of the SNAP-25 protein with the four cysteine residues highlighted by dotted rectangular boxes.
Figure 2:
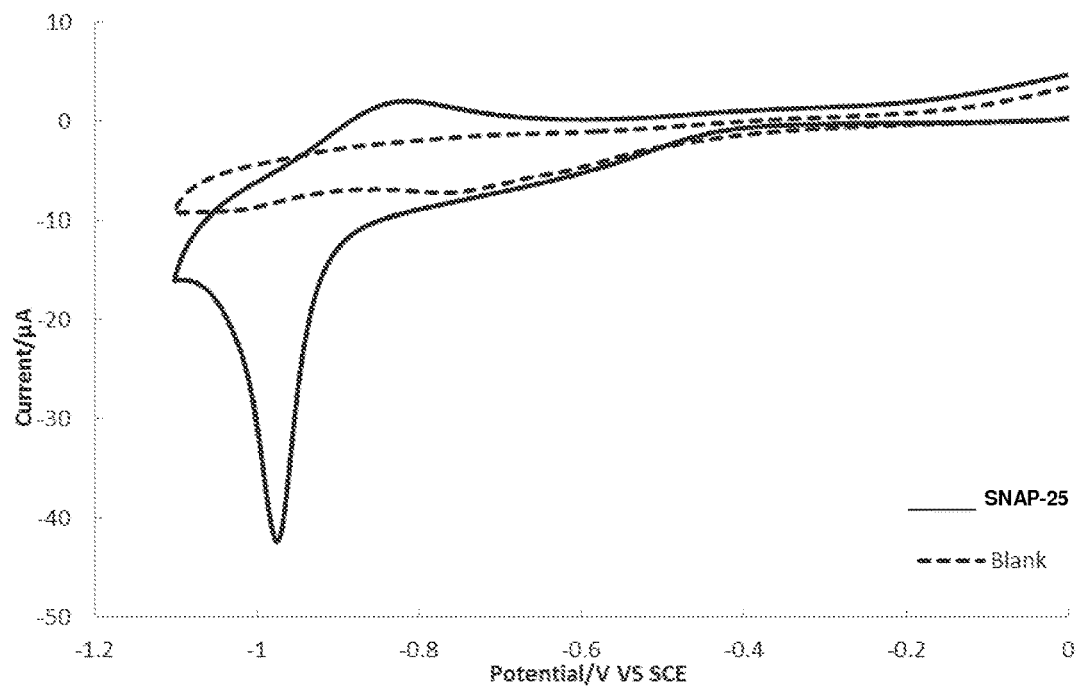
FIG. 2 is a cyclic voltammogram of SNAP-25 on a gold surface compared to a bare gold surface.

Botulinum neurotoxin A cleaves the protein SNAP-25 between the amino acid residues 197-198 (Y. Humeau, et al., (2000) *Biochimie*, 82, 427-446) leaving two lengths of protein. FIG. 1 shows SNAP-25 bound to the neuronal membrane via four cysteine residues (which are highlighted with dotted rectangular boxes). These cysteine residues allow the SNAP-25 to form a self-assembled monolayer on a gold surface as show in FIG. 2. The peak at −0.97 V is the cathodic peak characteristic of thiol desorption (K. Uosaki (2009) *The Chemical Record*. 9, 199-209), proving that SNAP-25 can form a monolayer on the gold. To form the monolayer the gold slides were annealed and left in the SNAP-25 solution at 5° C. for 48 hours, they were then removed from the solution and rinsed with purified water (18 MΩ).

Whilst the proof of principle experiments below were conducted with SNAP-25, it is envisaged that attaching VAMP and/or syntaxin proteins to the slides would also work with minimal modification. Furthermore, the provision of attaching a mixture of SNAP-25 and/or VAMP and/or syntaxin proteins would also enable the detection of a range of botulinum neurotoxin serotypes. SNAP-25 is cleaved by botulinum neurotoxin A, C and E; VAMP is cleaved by botulinum neurotoxin B, D, E, F and G; and syntaxin is cleaved by botulinum neurotoxin C—hence having a sensor or detection method which incorporates all of the proteins will allow the identification of all known serotypes of the toxin. Alternatively, using only a specific protein or proteins would enable targeting detection of more specific serotypes of interest in a given sample.

Example 1—UV-Vis Colloidal Gold

In this first experiment, gold colloids were coated with SNAP-25 peptides and then placed in a buffer solution which turned blue in colour when exposed to botulinum toxin.

Figure 3:
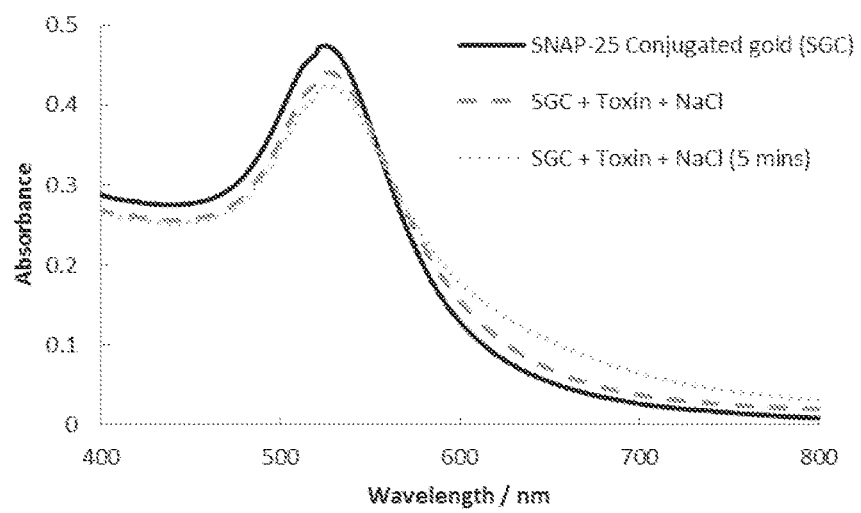
FIG. 3 is a UV-Vis spectroscopy of a toxin sample which had measured absorbance from 400 to 800 nm.

Gold colloids have a negative charge causing them to repel each other in solution staying red in colour absorbing at 525 nm. When NaCl is added to uncoated colloids, this neutralises the charges causing them to clump together turning blue in colour. Coating the colloids with substrates such as proteins protects from the neutralising charges keeping the colloids in solution. When the toxin is added a portion of SNAP-25 is cleaved off, which means the colloids are not as well protected allowing for the aggregation of colloid particles turning blue in colour absorbing in the 600-700 nm region. The following protocol was followed:
  a) Colloidal gold and phosphate buffer (10 mM, pH 8) solution were mixed in a 1:1 ratio and placed at 37° C. to equilibrate.
  b) SNAP-25 (0.5 μg/ml) was added to the solution and left on a shaker at 37° C. overnight so as to form SNAP-25 gold conjugates (SGC) (the SGC were kept at 37° C. throughout the experiment).
  c) The gold solution (960 μl) was added to a cuvette and the absorbance measured from 400 to 800 nm as shown in FIG. 3 (labelled SNAP-25 Conjugated gold (SGC)).
  d) The toxin sample (1 μl) was added and the solution mixed gently by pipetting, the absorbance was once again measured (results not shown) and the solution left to incubate for 5 minutes.
  e) NaCl (4 M, 40 μl) was then added and the absorbance measured (labelled SGC+Toxin+NaCl).
  f) The solution was left for a further 5 minutes before the absorbance was measured again (labelled SGC+Toxin+NaCl (5 mins)).

The change in absorbance at 525 and 670 nm were recorded and plotted against toxin concentration producing a correlation graph.

Figure 4:
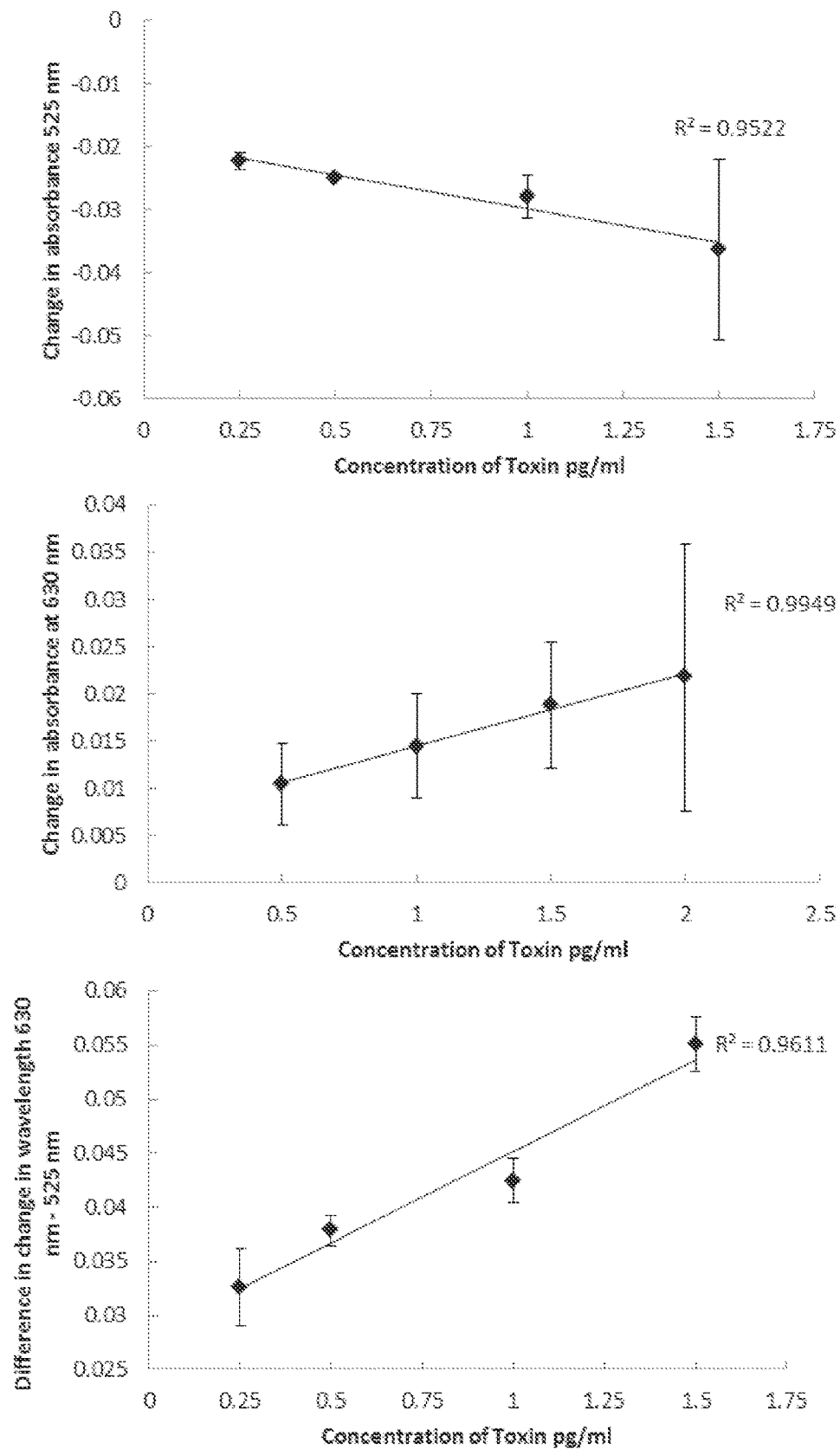
FIG. 4 shows correlation graphs for UV-vis spectroscopy of toxin where the plots show change in absorbance calculated from when the toxin was added to the end of the experiment.

The higher concentrations of toxin cleave more SNAP-25 making it more susceptible to precipitating from the solution on the addition on NaCl as shown in FIG. 4.

This experiment therefore illustrates that placing gold-SNAP-25 conjugates in a salt solution can act as a sensor for detecting and quantifying botulinum neurotoxin in a sample when used in conjunction with UV visible spectrometry.

Example 2—Electrochemical Impedance Spectroscopy

In this second experiment, gold electrodes were coated in SNAP-25 proteins. Rather than the SNAP-25 protein cleavage by the botulinum neurotoxin being detected by UV visible spectrometry, the cleavage event was detected by changes in impedance (Z) when the sample was placed in an electrochemical cell.

Impedance is a measure of a circuits ability to resist the flow of electrons in an alternating current. Using a redox probe the amount of oxidation/reduction can be measured at the gold surface. Forming the protein layer on the gold surface blocks some of the redox probe from approaching the surface and undergoing the redox reaction producing large impedance.

In this experiment, gold electrodes were annealed and incubated in a solution of SNAP-25 for 48 hours at 5° C. The electrodes were rinsed and dried before being sealed in an electrochemical cell and the impedance measured in redox probe (0.5 mM Ferri/Ferrocyanide, 0.1M KCl). The redox probe was removed and the sample diluted in ultra-pure water before being added to the gold surface. This was then incubated at 37° C. for 20 mins before the sample was removed and the impedance remeasured.

Figure 5:
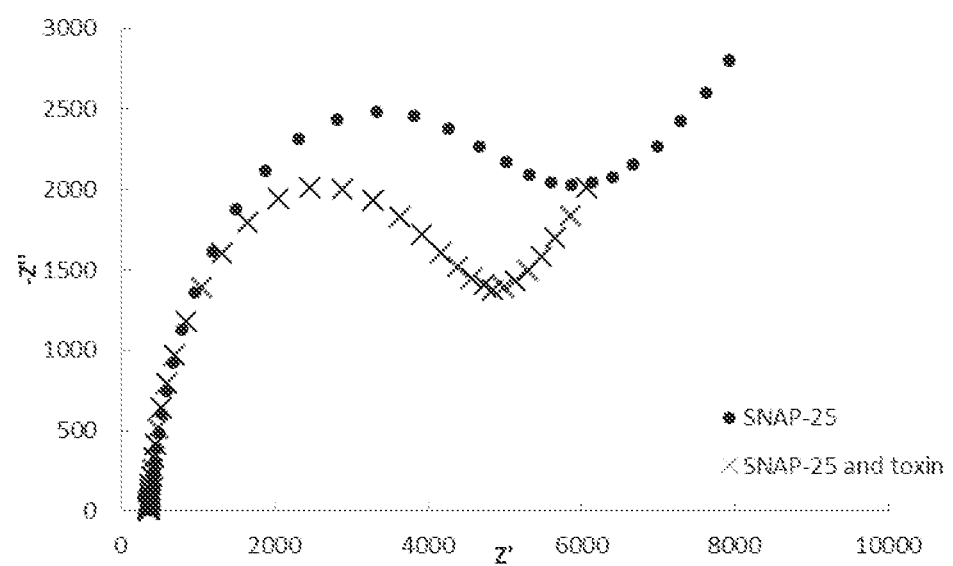
FIG. 5 shows EIS data for SNAP-25 before and after a toxin sample.

With the addition of the active toxin the protein at the electrode surface was decreased in size making it possible for more of the redox probe to reach the underlying electrode and reducing the impedance measured as shown in FIG. 5. When the placebo product was added instead of the toxin the impedance change produced was negligible.

The forgoing embodiments are not intended to limit the scope of the protection afforded by the claims, but rather to describe examples of how the invention may be put into practice.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety.

The invention claimed is:

1. A composition for detecting the presence of a botulinum neurotoxin in a sample, the composition comprising:
  a colloid formed from:
    (a) a salt solution;
    (b) charged particles suspended in the salt solution; and
    (c) a cleavable coating on the charged particles,
  wherein the cleavable coating comprises at least one SNAP-25, VAMP or syntaxin protein;
  wherein the composition has a first color when the cleavable coating is present on the charged particles suspended in the salt solution; and
  wherein the composition has a second color when the coating is cleaved.

2. The composition as claimed in claim 1, wherein the first color is red and the second color is blue.

3. A method of producing a sensor for detecting the presence of botulinum neurotoxin in a sample, the method comprising:
  (a) coating an electrically conductive substrate with a colloid formed from:
    a salt solution,
    charged particles suspended in the salt solution, and
    a cleavable coating on the charged particles, wherein the cleavable coating comprises at least one SNAP-25, VAMP or syntaxin protein,
wherein the composition has a first color when the cleavable coating is present on the charged particles suspended in the salt solution, and
wherein the composition has a second color when the coating is cleaved;
(b) providing a vessel in which the coating can be placed in contact with the sample and optionally other reagents; and
(c) providing a detection arrangement adapted to enable the detection of botulinum neurotoxin driven SNAP-25, VAMP or syntaxin cleavage events.

4. The method as claimed in claim 3, wherein the detection arrangement comprises a detector and the method further comprises:
(d) coupling the detector to a display for displaying the presence, and optionally the quantity, of the botulinum neurotoxin in the sample.

5. A method of detecting the presence of botulinum neurotoxin in a sample, the method comprising:
(a) providing the composition of claim 1;
(b) contacting the sample with the composition; and
(c) detecting whether the composition undergoes a visual change of color from the first color to the second color.

6. The method as claimed in claim 5, wherein the method further comprises the step of:
(d) quantifying the botulinum neurotoxin in the sample by detecting the number or quantity of SNAP-25, VAMP or syntaxin proteins which have been cleaved by the contacting step.

7. The method as claimed in claim 5, detecting whether the composition undergoes a visual change of color from the first color to the second color comprises detecting and measuring the difference in absorbance profile of the composition between 525-670 nm relative to a control absorbance profile.

8. The method as claimed in claim 5, wherein the charged particles are negatively charged.

9. A detection kit for detecting the presence of a botulinum neurotoxin in a sample, the kit comprising:
(i) a colloid formed from:
(a) a salt solution;
(b) charged particles suspended in the salt solution; and
(c) a cleavable coating on the charged particles,
wherein the cleavable coating comprises at least one SNAP-25, VAMP or syntaxin protein;
wherein the composition has a first color when the cleavable coating is present on the charged particles suspended in the salt solution; and
wherein the composition has a second color when the coating is cleaved; and
(ii) a color scale for assessing a visual color profile of a mixture of the salt solution and the sample between 525-670 nm.

10. The kit as claimed in claim 9, wherein the electrically conductive and negatively charged particles are coated with two or all of SNAP-25, VAMP and syntaxin proteins.

11. The kit as claimed in claim 9, wherein the charged particles are negatively charged.

12. The composition as claimed in claim 1, wherein the charged particles are negatively charged.

13. The composition as claimed in claim 12, wherein the charged particles are electrically conductive.

14. The kit as claimed in claim 11, wherein the charged particles are electrically conductive.

* * * * *